(12) United States Patent
Voto

(10) Patent No.: US 7,540,861 B1
(45) Date of Patent: Jun. 2, 2009

(54) WAFER RETAINING BELT FOR A COLOSTOMY BAG

(76) Inventor: Albert J. Voto, 20615 Bakal Dr., Riverside, CA (US) 92508-9201

(*) Notice: Subject to any disclaimer, the term of this patent is extended or adjusted under 35 U.S.C. 154(b) by 148 days.

(21) Appl. No.: 11/069,650

(22) Filed: Feb. 28, 2005

(51) Int. Cl.
*A61F 5/449* (2006.01)
(52) U.S. Cl. .................. 604/343; 604/344; 604/345
(58) Field of Classification Search .......... 604/332–345
See application file for complete search history.

(56) References Cited

U.S. PATENT DOCUMENTS

| | | | | |
|---|---|---|---|---|
| 1,217,567 | A * | 2/1917 | Clare | 604/343 |
| 2,423,060 | A * | 6/1947 | Zaro | 604/343 |
| 2,503,056 | A * | 4/1950 | Lay | 604/343 |
| 2,542,233 | A * | 2/1951 | Carroll | 604/337 |
| 2,555,086 | A * | 5/1951 | Guinn | 604/333 |
| 2,684,676 | A * | 7/1954 | Perry | 604/344 |
| 2,688,327 | A * | 9/1954 | Berg | 604/333 |
| 2,877,768 | A * | 3/1959 | Higgins | 604/343 |
| 2,928,393 | A * | 3/1960 | Marsan | 604/334 |
| 2,973,759 | A * | 3/1961 | Plymale, Jr. | 604/334 |
| 3,055,368 | A | 9/1962 | Baxter | |
| 3,123,074 | A * | 3/1964 | Turner | 604/332 |
| 3,351,061 | A | 11/1967 | Nolan | |
| 3,366,114 | A * | 1/1968 | Kanter | 604/336 |
| 3,398,744 | A * | 8/1968 | Hooper | 604/340 |
| 3,523,534 | A | 8/1970 | Nolan | |
| 3,557,790 | A * | 1/1971 | Hauser | 604/342 |
| 3,570,490 | A | 3/1971 | Berger | |
| 3,646,936 | A | 3/1972 | Marsan | |
| 3,667,469 | A * | 6/1972 | Marsan | 604/336 |
| 3,712,304 | A | 1/1973 | Marsan | |
| 3,759,260 | A | 9/1973 | Nolan et al. | |
| 3,773,048 | A | 11/1973 | Kirkliauskas | |
| 3,804,091 | A | 4/1974 | Nolan et al. | |
| 3,822,704 | A | 7/1974 | Nolan | |
| 3,841,332 | A | 10/1974 | Treacle | |
| 3,897,780 | A | 8/1975 | Trousil | |
| 3,898,990 | A | 8/1975 | Nolan | |
| 3,902,496 | A * | 9/1975 | Eakin | 604/334 |
| 3,948,256 | A * | 4/1976 | Schneider | 604/344 |
| 3,970,085 | A | 7/1976 | Mersan | |
| 4,078,567 | A * | 3/1978 | Fenton | 604/342 |
| 4,085,752 | A | 4/1978 | Canale | |
| 4,185,630 | A | 1/1980 | Neumeier et al. | |
| 4,209,023 | A | 6/1980 | Layton | |
| 4,211,224 | A | 7/1980 | Kubach et al. | |
| 4,213,458 | A | 7/1980 | Nolan et al. | |

(Continued)

FOREIGN PATENT DOCUMENTS

EP 0 320 895 6/1989

*Primary Examiner*—Tatyana Zalukaeva
*Assistant Examiner*—Paula L Craig
(74) *Attorney, Agent, or Firm*—Knobbe, Martens, Olson & Bear, LLP

(57) ABSTRACT

An assembly for use of the colostomy bag to inhibit the wafer from disengaging with the skin of the patient. This assembly includes a belt having a retaining member that is contoured to concentrate force adjacent an opening that allows access from the stoma to a collection bag for waste products to flow through. By contouring the retaining member of the belt in this fashion, the tendency of the wafer of the colostomy bag assembly to disengage from the skin of the patient is reduced.

7 Claims, 4 Drawing Sheets

U.S. PATENT DOCUMENTS

| | | | |
|---|---|---|---|
| 4,219,023 A * | 8/1980 | Galindo | 604/344 |
| 4,253,460 A | 3/1981 | Chen et al. | |
| 4,256,110 A * | 3/1981 | Scoville | 604/342 |
| 4,296,749 A | 10/1981 | Pontifex | |
| 4,386,931 A | 6/1983 | Nelson | |
| 4,387,712 A | 6/1983 | Briggs et al. | |
| 4,403,991 A | 9/1983 | Hill | |
| 4,411,659 A | 10/1983 | Jensen et al. | |
| 4,435,171 A * | 3/1984 | Goldberg et al. | 604/540 |
| 4,465,486 A | 8/1984 | Hill | |
| 4,551,888 A | 11/1985 | Beecher | |
| 4,701,169 A | 10/1987 | Steer | |
| 4,755,177 A | 7/1988 | Hill | |
| 4,865,594 A | 9/1989 | Thomas | |
| 5,013,307 A * | 5/1991 | Broida | 604/338 |
| 5,015,244 A | 5/1991 | Cross | |
| 5,026,362 A * | 6/1991 | Willett | 604/345 |
| 5,098,420 A | 3/1992 | Iacone | |
| 5,135,519 A * | 8/1992 | Helmer | 604/332 |
| 5,269,774 A | 12/1993 | Gray | |
| 5,338,315 A | 8/1994 | Baker | |
| 5,423,783 A | 6/1995 | Battles et al. | |
| D369,662 S | 5/1996 | Kuentz | |
| 5,626,570 A | 5/1997 | Gallo | |
| 5,653,701 A * | 8/1997 | Millman | 604/345 |
| 5,693,035 A | 12/1997 | Leise, Jr. et al. | |
| 5,865,820 A * | 2/1999 | Myello et al. | 604/345 |
| 5,938,647 A | 8/1999 | Smith | |
| 5,947,942 A | 9/1999 | Galjour | |
| 5,989,235 A | 11/1999 | Quacquarella et al. | |
| D418,221 S | 12/1999 | Betts et al. | |
| 6,186,989 B1 * | 2/2001 | Horie | 604/345 |
| 6,224,581 B1 | 5/2001 | Withers et al. | |
| 6,328,721 B1 | 12/2001 | Prohaska | |
| 6,679,866 B1 | 1/2004 | Gunawan | |
| 6,790,201 B2 * | 9/2004 | Meyer | 604/345 |
| 7,166,091 B1 * | 1/2007 | Zeltner | 604/345 |
| 2002/0010445 A1 | 1/2002 | Gunn | |
| 2003/0023210 A1 * | 1/2003 | Bedard et al. | 604/332 |
| 2003/0105438 A1 | 6/2003 | Hostetler | |

* cited by examiner

WAFER RETAINING BELT FOR A COLOSTOMY BAG

BACKGROUND OF THE INVENTION

1. Field of the Invention

The present invention relates to colostomy bag apparatus and, in particular, it concerns a belt assembly for helping to secure a wafer component of the colostomy bag apparatus in contact with the patient's skin.

2. Description of the Related Art

Colostomy are surgical procedures that require the removal of some or all of a patient's colon due to a variety of medical problems. When a colostomy is performed, the patient must then be provided with an alternative way of removing bodily waste from their intestinal tract. Typically, a portion of the intestinal tract is protruded through the patient's abdomen so as to form a stoma that extends out of the patient's skin. The waste products of the intestinal tract can then flow out of the stoma and be captured in a receptacle commonly referred to as a colostomy bag.

The typical colostomy bag apparatus currently in use includes a wafer component which is a disk that is coated with an adhesive on one side and has a hole that extends through the center of the wafer. The wafer is adhered to the skin surrounding the stoma such that the stoma protrudes through the hole. The wafer also preferably has a securing mechanism formed on the outer surface of the wafer that engages with a collection bag. The securing mechanism is preferably designed to allow for attachment and disengagement of collection bags from the wafer to thereby allow the patient to replace bags as they fill up. In use, the patient attaches a wafer to their skin using the adhesive such that the stoma protrudes through the wafer. The patient can then periodically attach collection bags to the wafer and remove them as the bags become full.

However, one problem that occurs with typical colostomy bag assembly is that the weight of the collection bag or the movement of the patient or both can result in the adhesive of the wafer becoming either partially or completely disengaged from the skin of the patient. This can cause several problems for the patient including leakage of the waste products. Even relatively small dislodgement of the adhesive from the skin surrounding the stoma allows for waste material to accumulate in the space between the dislodged wafer and the patient's skin. Over time, this can typically result in burns or other skin irritation which can become quite painful for the patient. Further, once the wafers become dislodged, the patient will have to replace the wafer which can result in repeated replacement of the wafer over the course of a week, e.g. 3-4 times, which adds greatly to the inconvenience of using a colostomy bag assembly.

In the past, belts have been devised for use in conjunction with colostomy bags. However, these belts are generally less effective in preventing the adhesive of the wafer from disengaging with the skin of the patient. In general, these belts are typically designed to either hide the bag from view or help support the weight of the full colostomy bag and are not specifically adapted to exert pressure on the wafer so as to maintain contact between the adhesive of the wafer and the patient's underlying skin. Other belts have been developed which exert pressure against the wafer, however these other belts are generally uncomfortable to wear or are not adaptable for use with currently available colostomy bag assembly.

For example, U.S. Pat. No. 5,947,942 to Galjour discloses one such belt assembly that has an inner belt which contacts the patch however, this belt assembly is actually comprised of two separate belts with a pouch contain therebetween which require the addition of separate interconnection apparatus to actually connect the stoma to the collection bag. The complication of the Galjour device results in greater complication for use of the colostomy bag assembly by the patient and further results in the patient having to wear a heavier, bulkier belt.

From the foregoing, there is a need for a light-weight, comfortable colostomy bag assembly that more readily secures the colostomy bag to the patient. To this end, there is a need for a colostomy bag assembly that concentrates pressure against the wafer to inhibit the wafer from detaching from the skin of the patient and is adaptable for use for currently available colostomy bag.

SUMMARY OF THE INVENTION

The aforementioned needs were satisfied by the colostomy bag assembly of the present invention which, in one aspect, comprises a belt that is adapted to be used with a wafer that adhesively attaches to the patient's skin and can be secured to a collection bag. In this implementation, the belt comprises a retaining member which is preferably formed of a light-weight flexible material and has an aperture formed therein so as to allow the collection bag to be coupled to the wafer to receive the waste product from the patient. The retaining member is sized and contoured so as to concentrate force against the perimeter of the wafer adjacent the stoma. The colostomy belt assembly further comprises two straps which are adapted to be positioned about the patient and exert force on the retaining member. In one particular implementation, the retaining member is dimensioned such that tightening of the straps results in an inward force being exerted by the retaining member on the wafer to thereby inhibit the wafer from dislodging from the skin of the patient. In one implementation, the retaining member has a rectangular section having a first width and height. The retaining member further has a generally triangular or trapezoid shaped section attached to either end of the rectangular section. The straps are then attached to the generally triangular shaped section. By tapering the retaining member from a widest point, adjacent where the retaining member engages the wafer and the place where the straps attach to the retaining member, a tightening force on the straps results in the retaining member, which in one implementation is made of a flexible fabric, exerting greater inward force on the wafer.

Moreover, by forming the retaining member out of a flexible material the belt better matches the contours of the patient's skin such that the movement of the patient is less likely to result in the belt disengaging from the wafer thereby allowing the wafer to disengage from the patient's skin. Further, the use of a flexible material, such as vinyl or felt covered vinyl, for the retaining member allows for a relatively thin single layer belt that is comfortable for the patient to wear. These and other objects and advantages of the present invention will become more apparent from the following description taken in conjunction with the accompanying drawings.

DETAILED DESCRIPTION OF THE PREFERRED EMBODIMENT

Figure 1:
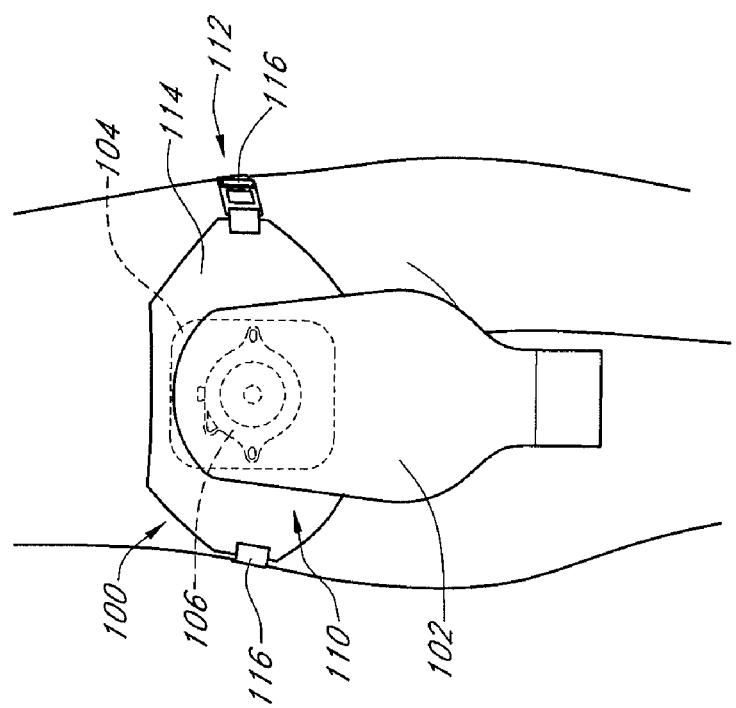
FIG. 1 is a front isometric view of the wafer retaining belt for a colostomy bag of the illustrated embodiment.

Reference will now be made to the drawings wherein like numerals refer to like parts throughout. FIG. 1 is a perspective view of a colostomy bag retaining assembly 100 of the illustrated embodiment. In this particular implementation, the colostomy bag retaining assembly 100 include a collection bag 102 that is attached to a wafer 104 via a known securing mechanism 106 in a manner that will be described in greater detail below. The wafer 104 is adhered to the patient's skin with a stoma extending through an opening so as to allow body waste to flow in to the collection bag 102.

As is also illustrated in FIG. 1, a securing belt 110 is secured about the patient's waist 112 so as to be interposed between the receptacle bag 102 and the wafer 104. The securing belt 110 comprises a retaining member 114 and belt straps 116 that are attached to the outer edges of the retaining member 114 so as to exert an inward force against the wafer 104 when the straps 116 are tightened to thereby induce the wafer 104 to be urged up against the skin of the patient. In this way, dislodgement of the wafer 104 from the skin of the patient is inhibited which thereby inhibit leakage the waste fluid adjacent the skin of the patient.

Figure 2:
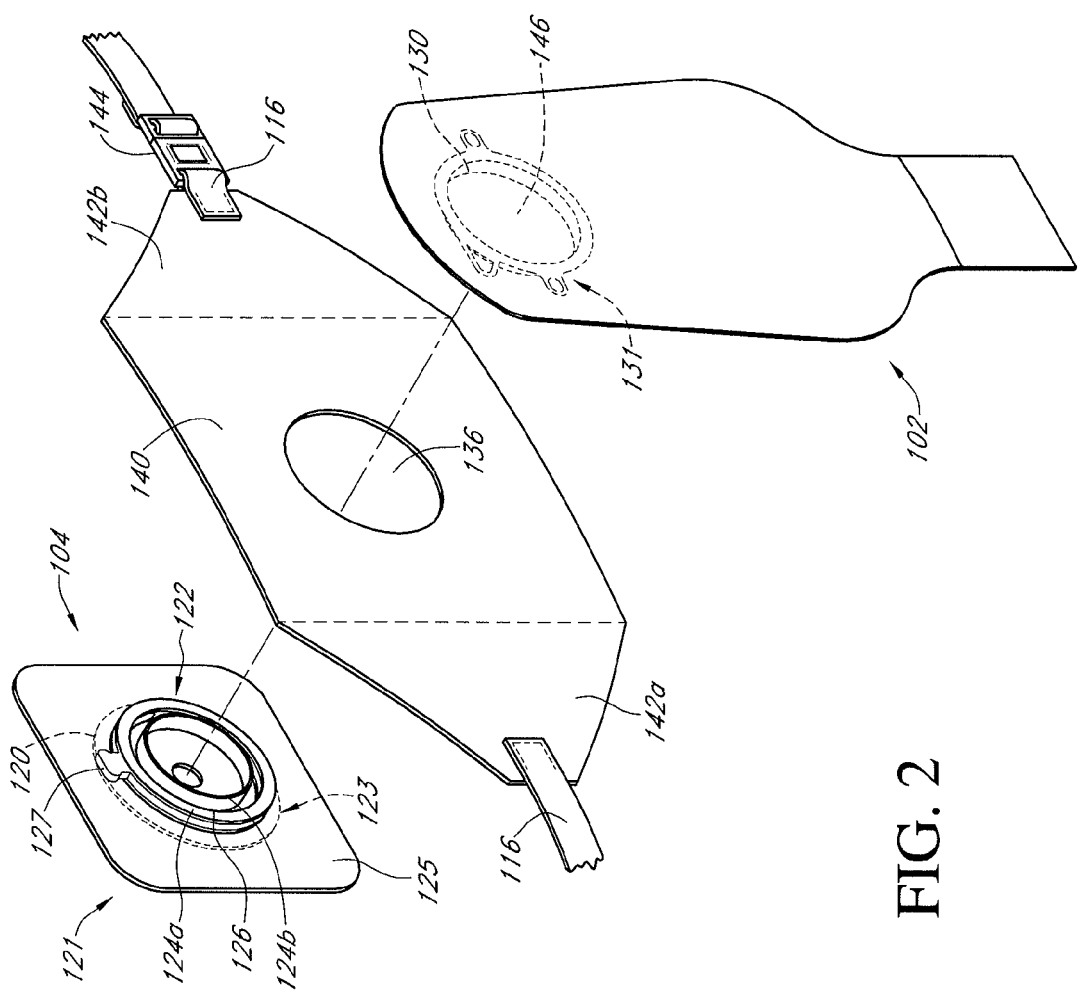
FIG. 2 is an exploded perspective view of the assembly of FIG. 1.

FIG. 2 is an exploded perspective view of the assembly 100 that shows the various components of the assembly in greater detail. In particular, the wafer 104 comprise an adhesive pad 120 that is adhered to the skin of the patient via an adhesive positioned on an inner side 121 of the pad 120. On the outer surface 123 of the adhesive pad 120, there is a securing mechanism 122 that secures the wafer 106 to the collection bag 102. In this implementation the pad has a diameter of approximately 3 inches. In this embodiment the securing mechanism 122 comprises two annular rings 124a, 124b that define a groove 126 interposed therebetween. An annular protrusion 130 on the connection mechanism 106 of receptacle bag 102 is positioned in the groove 126 and is secured thereto by a plurality of locking members formed on the annular rings 124a, 124b. The operation of the connection mechanism 106 is known in the art. The locking members are activated by a knob 127 to thereby allow the patient to periodically detach the collection bag 102 and replace it with a new bag 102.

As is also shown in FIG. 2, the wafer 102 also includes an additional adhesive layer 125 that is interposed between the adhesive pad 120 and the securing mechanism 122. The additional adhesive layer 125 is generally square in shape with dimensions of approximately 4 inches by 4 inches in this implementation, and serves to further secure the adhesive layer 120 to the skin of the patient. Specifically, the additional adhesive layer 125 adheres to both the outer surface of the adhesive pad 120 and the skin of the patient such that the outer periphery of the adhesive pad 120 is encapsulated within a pocket defined by the skin of the patient and the additional adhesive layer 125 adhering to the skin of the patient. The additional adhesive layer 125 thereby inhibits the outer periphery of the adhesive pad 120 from lifting away from the skin of the patient and further secures the wafer 104 to the patient.

As is also illustrated in FIG. 2, an opening 132 is formed in the center of the wafer 104 and the opening 132 is adapted to fit around the stoma 134 (See FIG. 4) of the patient to thereby allow waste material from the patient to flow through the wafer 104 and into the receptacle bag 102.

As is also shown in FIG. 2, the retaining member 114 of the securing belt 110 includes an opening 136 that is sized so as to allow the securing mechanism 122 of the wafer 104 to extend therethrough. Preferably, the inner edges of the opening 122 are positioned flush adjacent the locking mechanism 122 when the securing belt 110 is worn by the patient to thereby exert greater force against the wafer to ensure that the wafer 104 remains in contact with the patient's skin in the manner that will be described in greater detail below.

As is generally illustrated in FIG. 2, the opening 136 is preferably positioned within a generally rectangular section 140 of the retaining member 114 of the belt 110. At either ends of the rectangular section 140, the retaining member 114 of the securing belt 110 include two generally tapered, e.g., triangle or trapezoid shaped sections 142a, 142b. At the ends of the tapered sections 142a, 142b, the belt straps 116 are attached. As will be described in greater detail below, the configuration of the rectangular section 140 and the generally tapered shaped sections 142a, 142b of the retaining member 114 are designed to exert greater force on the regions of the rectangular section of 140 adjacent the opening 136 to thereby increase the amount of force that is being exerted against the wafer 104 to inhibit the adhesive pad 120 of the wafer 104 disengaging with the skin of the patient.

As is also illustrated in FIG. 2, the belt straps 116 include a clip or buckle assembly 144 of a type known in the art that allows the patient to secure the belt 110 about their waist and also to tighten the straps 116 to thereby increase the amount of force that is being exerted against the wafer 104 to ensure the wafer remains in contact with the patient's skin.

As shown in FIG. 2, the collection bag 102 includes a securing mechanism 131 that engages with the securing mechanism 122 of the wafer in the manner described above. The collection bag 102 also defines a hollow space that is adapted to receive waste fluids from the stoma 134 of the patient. Periodically, the collection bag 102 will fill at which time the patient will disengage the collection bag 102 from the wafer 104 and discard the bag. The bag 102 will then be replaced by a new bag 102 which will be reattached to the wafer 104 through the opening 136 of the retaining member 114 of the securing belt 110 without, generally requiring the removal of the wafer 104 or the securing belt 110.

Figure 3:
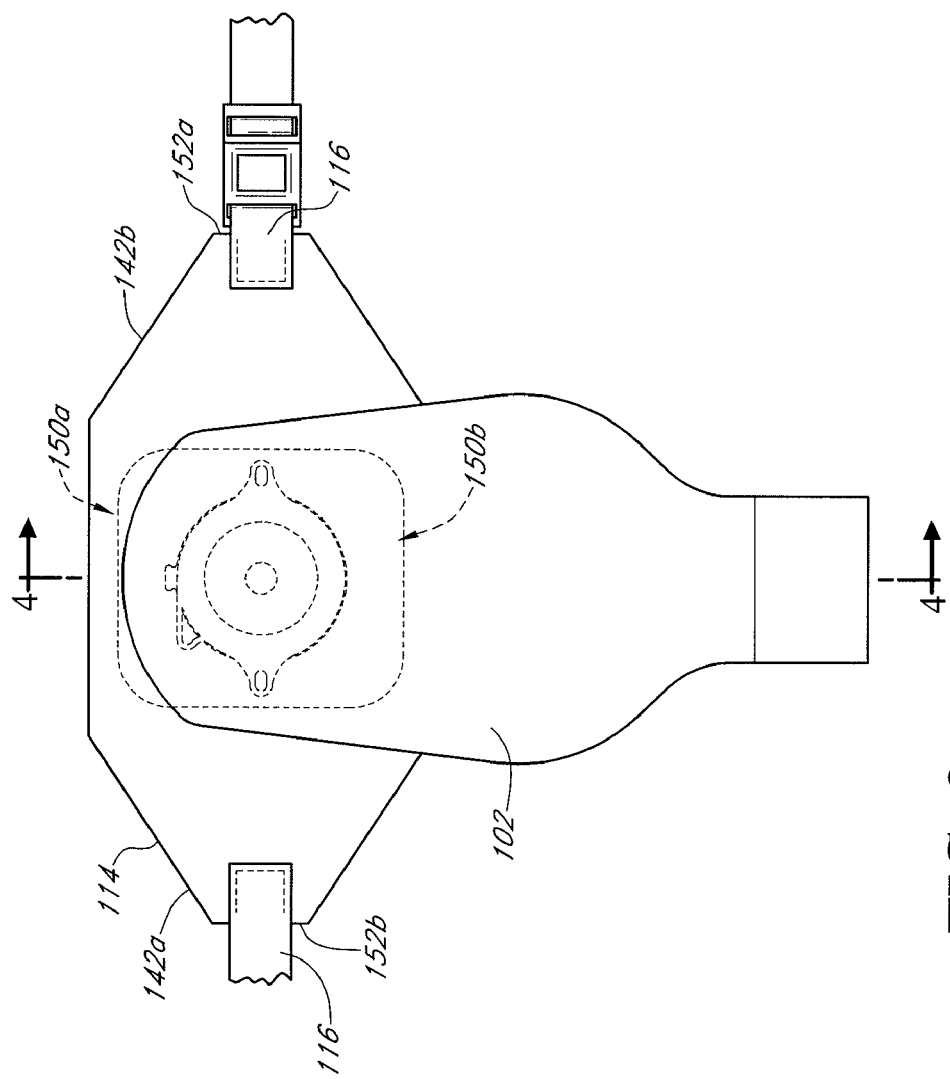
FIG. 3 is a front elevational view of the assembly of FIG. 1.

FIG. 3 is a front perspective view which illustrate the retaining member 114 in greater detail. Preferentially, the retaining member 114 is contoured such that as the person tightens the straps 116 to secure the belt 110 about the patient's waist 112, the transversely extending forces on the straps 116 result in a greater amount of the force being urged against the portions of the retaining member 114 immediately adjacent the opening 136. Consequently, the retaining section 114 is urged against the wafer 104 at the regions immediately adjacent the opening 136 to thereby exert greater force against the wafer 104 at the point where the wafer 104 is adhered to the patient's skin about the stoma 134.

In particular, as a result of the tapering of the trapezoidal sections 142a, 142b of the retaining section 114 of the belt 110, the inward force is concentrated in the regions 150a, 150b immediately about the opening 136. The concentration of force is a result of the geometry of the retaining section in that the tapering of the trapezoidal sections 142a, 142b concentrate the force in the regions 150a, 150b.

In one particular implementation, the rectangular section 140 of the retaining member 114 is approximately 4.5 inches extending between the tapering sections 142a, 142b. Moreover, the height of the rectangular section 140 is approximately 5.5 inches. The opening 136 in this implementation is approximately 2 inches in diameter. In this particular implementation, the tapered sections 142a, 142b extend approximately 3 inches out to an outer edge 152a, 152b which is approximately 1.5 inches wide. The belt straps 116 in this particular implementation are approximately 1 inch wide and are preferably centered on the edges 152a, 152b. Thus, the narrower straps 116 and the generally tapered sections 142a, 142b channels the inward force on the retaining section 114 towards the regions 150a, 150b to thereby enhance the force being exerted against the wafer 104 to inhibit the wafer from dislodging.

As indicated in FIG. 3, the straps 116 are generally centered about the opening 136 in the retaining section 114 and the width of the straps 116 is also substantially less than the diameter of the opening 136. When the straps 116 are placed around the patient tightened, the lines of force attempts to travel straight through the retaining member 114 between the straps 116. However, the opening 136 diverts the lines of force to the regions 150a, 150b. Since the retaining member 114 is positioned about a convex surface, e.g., the skin of the patient, the lines of force urge the regions 150a, 150b toward the opening 136 and also inward toward the patient thereby enhancing the force exerted on the wafer 104. By tapering the regions 142a, 142b the force of the straps is more directly transferred to the regions 150a, 150b.

In this particular implementation, the width of the straps 116 is approximately one half the diameter of the opening. Moreover, the edges 152a, 152b of the tapered regions 142a, 142b are approximately the same size as the width of the straps 116 e.g., the straps are approximately at least ⅔ the size of the edges 152a, 152b. The size of the regions 150a, 150b are also sized so as to increase the amount of force being exerted on the wafer 104 being large enough to cover the additional adhesive layer 105. Designing the retaining member 114 and the straps 116 in this fashion increases the amount of force that is exerted on the wafer thereby improving the retention characteristics over existing straps of the prior art.

Figure 4:
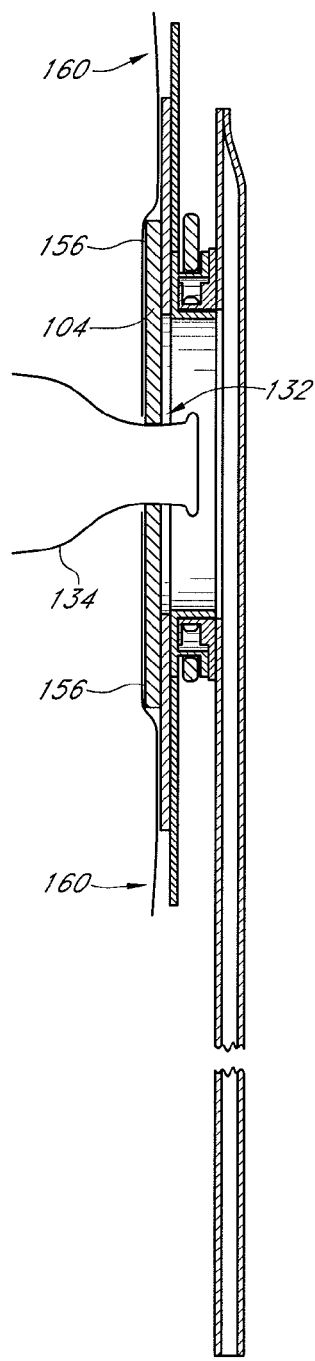
FIG. 4 is a cross-sectional view of the assembly of FIG. 3 taken along the lines 4-4.

FIG. 4 shows a cross-section of the assembly 100 in greater detail as it is attached to the patient. As indicated, the wafer 104 is adhered to the skin 160 of the patient that surrounds the surgically created stoma 134 while the stoma 134 extending through the opening 132 in the wafer 104. As is shown in FIG. 4 an annular portion 156 of the adhesive pad 120 extends beyond the securing mechanism 122 and thereby is contacted by the regions 150a, 150b of the retaining section 114 of the belt 110. Moreover, as is also illustrated in FIG. 4, the additional adhesive layer 125 is substantially continuously contacted by the retaining member 114 of the belt 110 so as to also urge the additional adhesive layer 125 against the skin of the patient. As is indicated, substantially all of the additional adhesive layer 125 is covered by the retaining section 114 of the securing belt 110 to thereby inhibit dislodgement of the additional adhesive layer 125 which thereby inhibits the outer periphery of the adhesive pad 120 from disengaging with the skin of the patient. The combination of the increased force exerted against the annular region 156 of the adhesive pad 120 and the substantially continuous engagement of the additional adhesive layer 125 further inhibits the wafer 104 from becoming dislodged from the skin of the patient about the stoma. Moreover, as the retaining member 114 is preferably performed of a light-weight flexible material, such as vinyl or felt covered vinyl, the fabric conforms to the general contour and configuration of the wafer 104 and additional adhesive layer 125 as it is positioned on the patient's skin so as to substantially uniformly exert an inward force as the belt is tightened.

From the foregoing, it would be appreciated that the illustrated embodiment provide a colostomy bag retaining assembly which exerts greater pressure against the wafer 104 so as to inhibit the wafer 104 from dislodging itself from the skin of the patient. Moreover, as the retaining section 114 is made of a generally light weight cloth material, the force can be uniformly applied against the wafer 104 to thereby enhance the ability of the retaining section 114 to inhibit the wafer 104 from dislodging from the skin of the patient but is also more comfortable to wear. By inhibiting the wafer 104 from removing from the skin of the patient, there is less likelihood that waste fluids from the patient will seep into the area between the wafer 104 and the skin thereby causing irritation for the patient.

Although the illustrated embodiment of the present invention is shown, described and pointed out the fundamental novel features of the invention as applied to this embodiment, it will be understood that various omissions, substitutions, and changes in the form of the detail of the device illustrated may be made by those skilled in the art without departing from the spirit of the present invention. Consequently the scope of the invention should not be limited to the foregoing description which should be defined by the appended claims.

What is claimed is:

1. A colostomy bag assembly comprising:
   a wafer having an adhesive pad and an opening extending therethrough wherein the adhesive pad attaches to the skin of a patient so as to allow a stoma of the patient to extend through the opening;
   a securing mechanism formed on the wafer;
   a collection bag that couples to the securing mechanism so as to be secured to the wafer wherein the collection bag receives waste fluids from the stoma when secured to the wafer via the securing mechanism;
   a retaining member that has an opening sized to fit around the securing mechanism attached to the wafer such that the retaining member is interposed between the collection bag and the wafer wherein the retaining member is made of a flexible cloth material;
   a plurality of straps, the straps defining a belt, the straps being attached to the retaining member wherein the straps are positioned so as to be aligned with the opening in the retaining member and are sized to have a width substantially smaller than the diameter of the opening such that when the patient positions the retaining member in between the wafer and the collection bag and secure the straps to each other, the straps induce the retaining member to concentrate force in the regions immediately above and below the opening in the retaining member to thereby inhibit the wafer positioned underneath the retaining member from disengaging with the skin of the patient;
   wherein the width of each of the straps is approximately one half the diameter of the opening of the retaining member and the straps are substantially centered with respect to the opening; and
   wherein the retaining member has a central, generally rectangular section and two tapered sections, each tapered section being trapezoidal in shape, and wherein the straps are coupled to the ends of the two tapered sections respectively and wherein the width of the ends of the tapered sections is substantially approximate the width of the straps and wherein the shape of the tapered section results in greater force being exerted against the wafer by the central section as a result of tightening the belt.

2. The assembly of claim 1, wherein the flexible cloth material of the retaining member comprises vinyl.

3. The assembly of claim 1, wherein the opening in the retaining member has a diameter of approximately 2 inches.

4. The apparatus of claim 1, the widths of the ends of the tapered sections are approximately 1.5 inches.

5. The apparatus of claim 4, wherein the central section is approximately 4.5 inches by 5.5 inches high and the tapered section extends approximately 3 inches from the central section.

6. The apparatus of claim 1, wherein the plurality of straps include a buckle assembly that allows the patient to tighten the straps about their waist to thereby increase the inward force on the wafer.

7. The apparatus of claim 1, wherein the retaining member is sized so as to substantially contact the entire exposed area of a second adhesive layer such that the second adhesive layer is urged in contact with the skin of the patient to thereby encapsulate the adhesive pad of the wafer between the second adhesive layer and the patient's skin.

* * * * *